United States Patent
Handa (10) Patent No.: US 10,209,207 B2
(45) Date of Patent: Feb. 19, 2019

(54) X-RAY TALBOT INTERFEROMETER

(71) Applicant: CANON KABUSHIKI KAISHA, Tokyo (JP)

(72) Inventor: Soichiro Handa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 122 days.

(21) Appl. No.: 15/226,667

(22) Filed: Aug. 2, 2016

(65) Prior Publication Data

US 2017/0038318 A1   Feb. 9, 2017

(30) Foreign Application Priority Data

Aug. 5, 2015   (JP) ................... 2015-155461

(51) Int. Cl.
| | |
|---|---|
| *G03H 5/00* | (2006.01) |
| *G01N 23/20* | (2018.01) |
| *A61B 6/00* | (2006.01) |
| *G21K 1/02* | (2006.01) |

(52) U.S. Cl.
CPC ....... *G01N 23/20075* (2013.01); *A61B 6/484* (2013.01); *G21K 1/02* (2013.01); *A61B 6/4035* (2013.01); *A61B 6/4291* (2013.01); *G21K 2207/005* (2013.01)

(58) Field of Classification Search
CPC ..... A61B 6/484; A61B 6/4291; A61B 6/4035; G01N 23/20075
See application file for complete search history.

(56) References Cited

U.S. PATENT DOCUMENTS

| | | | |
|---|---|---|---|
| 9,700,267 B2 * | 7/2017 | Baturin | ........... A61B 6/4035 |
| 2012/0236985 A1 * | 9/2012 | Schusser | ............. G21K 1/06 378/16 |

(Continued)

FOREIGN PATENT DOCUMENTS

| | | |
|---|---|---|
| JP | 2011-153869 A | 8/2011 |
| JP | 5162453 B2 | 3/2013 |

OTHER PUBLICATIONS

Nesterets et al., "Phase-contrast imaging using a scanning-double-grating configuration", Optics Express, Apr. 14, 2008, vol. 16, No. 8, pp. 5849-5867.

*Primary Examiner* — Kenneth J Malkowski
(74) *Attorney, Agent, or Firm* — Canon U.S.A., Inc. I.P. Division (57) ABSTRACT

An X-ray Talbot interferometer includes a source grating having a plurality of X-ray transmitting portions to transmit some X-rays from an X-ray source, a beam splitter grating configured to diffract the X-rays from the X-ray transmitting portions with a periodic structure to form interference patterns, an analyzer grating configured to block parts of the interference patterns, and a detector configured to detect X-rays from the analyzer grating. The X-ray transmitting portions of the source grating are arranged to form a periodic pattern in which spatial frequency components contained in a sideband resulting from modulation caused by the presence of an object are enhanced by superimposing the interference patterns corresponding to the respective X-ray transmitting portions. In the absence of any object, the positional relation between the periodic pattern and the grating pattern of the analyzer grating is substantially the same over the entire imaging field.

21 Claims, 4 Drawing Sheets

(56) References Cited

U.S. PATENT DOCUMENTS

2014/0146945 A1* 5/2014 Fredenberg .......... A61B 6/4233
378/62
2014/0270060 A1* 9/2014 Date ................ G01N 23/20075
378/36

* cited by examiner

X-RAY TALBOT INTERFEROMETER

BACKGROUND OF THE INVENTION

Field of the Invention

The present invention relates to an X-ray Talbot interferometer.

Description of the Related Art

An X-ray phase imaging technique is an imaging technique using phase changes that occur as X-rays pass through an object. Examples of X-ray phase imaging techniques that have been proposed include a Talbot interferometer described in Japanese Patent No. 5162453. The Talbot interferometer typically includes two or three gratings each having a periodic structure. Of these gratings, a grating normally disposed near the object may be referred to as a beam splitter grating, a grating normally disposed near a detector may be referred to as an analyzer grating, and a grating normally disposed near an X-ray source may be referred to as a source grating. These gratings may each be either a grating having a one-dimensional periodic pattern, or a grating having a two-dimensional periodic pattern. The detector is normally one that is capable of acquiring a two-dimensional intensity distribution of X-rays incident on the detection surface of the detector.

The beam splitter grating is typically a phase-modulation transmissive diffraction grating. X-rays incident on the beam splitter grating are diffracted by the periodic structure of the grating to form an interference pattern (also called a self-image of the grating) at a predetermined position by a so-called Talbot effect. Since the interference pattern is deformed reflecting, for example, phase changes that occur as X-rays pass through the object, information about the shape and internal structure of the object can be obtained by measuring and analyzing the intensity distribution of the interference pattern.

The analyzer grating is typically a grating that has a periodic transmittance distribution, because of the periodic arrangement of X-ray transmitting portions and X-ray shielding portions. The analyzer grating is disposed at the position of the interference pattern, and thus is used for the purpose of producing moire in the intensity distribution of X-rays transmitted through the grating. The moire reflects the deformation of the interference pattern, and the period of the moire can be increased infinitely. Therefore, even when the spatial resolution of the detector to be used is not high enough to allow direct detection of the interference pattern, information about the interference pattern can be indirectly obtained by detecting moire having a large pattern period.

Like the typical analyzer grating described above, the source grating is a grating having a structure where X-ray transmitting portions and X-ray shielding portions are periodically arranged. The source grating is normally disposed near an X-ray emitting spot in the X-ray source (X-ray generator), and used for the purpose of virtually forming an array of linear X-ray-emitting portions (or small X-ray-emitting spots in the case of a two-dimensional grating). A plurality of interference patterns formed by X-rays emitted from the linear X-ray-emitting portions are superimposed while displaced from each other by an integral multiple of the pattern period, in the absence of any object in the X-ray path. Thus, there is no pattern loss even when many interference patterns are superimposed, and it is possible to form a periodic pattern having generally high X-ray intensity and fringe visibility. To achieve the superimposition described above, the grating period of each grating and the distance between gratings need to be designed to meet certain conditions. A Talbot interferometer using the source grating described above may be specifically referred to as a Talbot-Lau interferometer. A Talbot interferometer using the source grating described above is disclosed in Japanese Patent No. 5162453. Hereinafter, the term "Talbot interferometer" includes a Talbot-Lau interferometer.

In an imaging technique using a Talbot interferometer, detection of interference patterns or moire patterns by a detector is generally followed by analysis of the detected patterns for conversion to a more useful image. Another imaging technique is known, in which a positional relation between gratings during imaging is designed to meet specific conditions, so that a detected special moire image can be directly used as an object image. For example, in imaging techniques described in Japanese Patent No. 5162453 and "Phase-contrast imaging using a scanning-double-grating configuration", OPTICS EXPRESS (US), 2008, Vol. 16, No. 8, pp. 5849-5867, by Y. I. Nesterets and S. W. Wilkins, imaging is performed by forming moire with a very large (ideally infinite) period, using an interferometer having a grating arrangement where an interference pattern and an analyzer grating pattern are precisely the same in direction and pitch. Here, a periodic pattern having the same period as the interference pattern may be formed on a detector, or no periodic pattern may be formed on the detector. In either case, an X-ray intensity acquired by each of a plurality of pixels of the detector is substantially the same. That is, the intensity distribution acquired by the detector is substantially uniform.

The document by Y. I. Nesterets and S. W. Wilkins describes a technique in which the relative positions of gratings are adjusted such that the intensity of X-rays transmitted through the gratings is minimized in the imaging region. Then, with the beam splitter grating and the analyzer grating fixed to each other, imaging is performed while both the gratings are being scanned at the same time. With this technique, the detector can acquire an image which strongly reflects not only absorption information of the object, but also scattering information (small-angle X-ray scattering power by microparticles, fine fibers, edges of structures, etc.) along the periodic direction of the interference pattern. In this technique, differential phase information along the periodic direction of the interference pattern is strongly reflected in the image if differential phase values are large and the local phase of interference fringes is sufficiently significantly shifted, but is not strongly reflected in the image if the local phase shift is not significant enough. In other words, the image obtained by the detector does not have high sensitivity to differential phase information. Even when imaging is performed without scanning of the two gratings, the resulting image will be substantially the same if the spatial resolution of the imaging system is not particularly high. This imaging technique which performs imaging, with the grating positions adjusted to minimize the intensity of X-rays transmitted through the gratings, is similar to a so-called dark-field technique in an optical microscope. In the present specification, an imaging technique which performs imaging with such grating positions (not based on the assumption of scanning of gratings) may be referred to as a dark-field technique. Conversely, an imaging technique which performs imaging, with the relative positions of gratings adjusted such that the intensity of X-rays transmitted through the gratings is maximized in the imaging region, may be referred to as a bright-field technique in the present specification.

Japanese Patent No. 5162453 describes a technique which performs imaging, with the relative positions of gratings adjusted such that the intensity of X-rays transmitted through the gratings is about the average of maximum and minimum values throughout the imaging region. In the present specification, this imaging technique may be referred to as an intermediate technique. With the intermediate technique, the detector can acquire an image which strongly reflects not only absorption information of the object, but also differential phase information (spatial differential values of the phase distribution of X-rays transmitted through the object) along the periodic direction of the interference pattern. However, with the intermediate technique, the detector can acquire very little scattering information of the object.

In the present specification, a phase distribution of X-rays transmitted through the object, a differential phase distribution obtained by spatially differentiating the phase distribution, and a secondary differential phase distribution obtained by differentiating the differential phase distribution in the same direction may be collectively referred to as phase information of the object.

With the use of a Talbot interferometer, when imaging is performed under conditions where the intensity distribution of X-rays transmitted through gratings is uniform in the imaging field, it is possible to acquire an image which strongly reflects not only the absorption information of the object, but also the phase information and the scattering information of the object. However, as described above, a Talbot interferometer which performs the intermediate technique is unable to acquire scattering information of the object. Also, a Talbot interferometer which performs the dark-field technique has low sensitivity to phase information of the object.

SUMMARY OF THE INVENTION

The present invention provides an X-ray Talbot interferometer that is capable of acquiring scattering information, and also acquiring phase information with higher sensitivity than a Talbot interferometer of the related art which performs the dark-field technique.

An X-ray Talbot interferometer according to an aspect of the present invention includes a source grating having a plurality of X-ray transmitting portions to transmit some X-rays from an X-ray source, a beam splitter grating configured to diffract the X-rays from the X-ray transmitting portions with a periodic structure to form interference patterns, an analyzer grating configured to block parts of the interference patterns, and a detector configured to detect X-rays from the analyzer grating. The beam splitter grating forms the interference patterns corresponding to the respective X-ray transmitting portions by diffracting X-rays from each of the X-ray transmitting portions with the periodic structure. The X-ray transmitting portions are arranged to form a periodic pattern in which specific spatial frequency components are enhanced by superimposing the interference patterns corresponding to the respective X-ray transmitting portions. The specific spatial frequency components are spatial frequency components contained in a sideband produced when spatial frequency components specific to the interference patterns are modulated by an object. When no object is placed between the source grating and the analyzer grating, a positional relation between the periodic pattern and a grating pattern of the analyzer grating is substantially the same over an entire imaging field.

Further features of the present invention will become apparent from the following description of exemplary embodiments with reference to the attached drawings.

DESCRIPTION OF THE EMBODIMENTS

Embodiments of the present invention will be described in detail with reference to the attached drawings. The same components are denoted by the same reference numerals throughout the drawings, and redundant description will be omitted. Because many X-ray Talbot interferometers (which may hereinafter be simply referred to as interferometers) use simple one-dimensional fringe interference patterns and an analyzer grating having a simple one-dimensional fringe pattern, the present embodiment will be described on the basis of such an interferometer configuration.

In an X-ray Talbot-Lau interferometer of the related art, a source grating is configured to enhance carrier components in interference patterns. In other words, the interferometer of the related art has a configuration in which interference patterns formed by respective small X-ray sources of an X-ray source array virtually formed by the source grating are superimposed such that bright portions are superimposed on each other and dark portions are also superimposed on each other, whereby the contrast between bright and dark portions is enhanced. On the other hand, an interferometer of the present embodiment is configured such that parts of bright portions of interference patterns are superimposed on each other, and parts of bright portions and parts of dark portions of the interference patterns are also superimposed on each other. Thus, in the Talbot-Lau interferometer of the present embodiment, the source grating enhances specific frequency components shifted from carrier waves of the interference patterns. The details will now be described.

Figure 4:
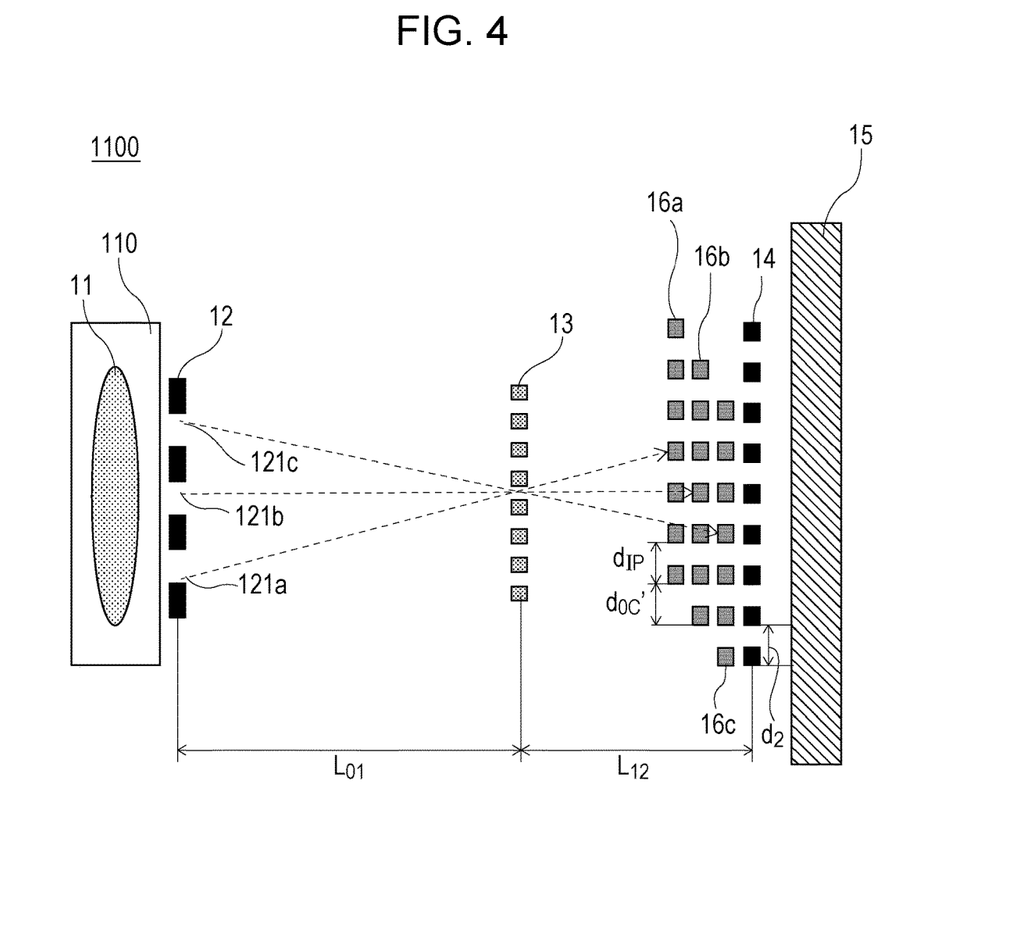
FIG. 4 is a schematic diagram of an X-ray Talbot interferometer according to a comparative example.

FIG. 4 is a schematic diagram of an X-ray Talbot-Lau interferometer 1100 of a comparative example, which is an X-ray Talbot-Lau interferometer of the related art. The X-ray Talbot-Lau interferometer 1100 includes an X-ray source 110 having an X-ray emitting spot (so-called focus) 11, a source grating 12, a beam splitter grating 13, an analyzer grating 14, and a detector 15. While not shown, an object is placed near the beam splitter grating 13 for imaging. The object may be placed either upstream of the beam splitter grating 13 (i.e., between the source grating 12 and the beam splitter grating 13), or downstream of the beam splitter grating 13 (i.e., between the beam splitter grating 13 and the analyzer grating 14).

In the X-ray Talbot-Lau interferometer 1100 of the related art, when no object is placed in the X-ray path, interference patterns 16a to 16c formed by X-rays transmitted through X-ray transmitting portions 121a to 121c of the source grating 12 are superimposed while displaced from each other exactly by an interference pattern period $d_{IP}$. That is, a relative displacement $d_{OC}'$ between a plurality of interference patterns superimposed on each other is equal to $d_{IP}$.

Thus, the interference patterns 16a to 16c formed by X-rays from the X-ray transmitting portions 121a to 121c are superimposed to allow exact coincidence between their bright portions and also between their dark portions. Thus, a high-intensity periodic pattern (which is formed by superimposing a plurality of interference patterns) having the same visibility as an interference pattern formed by X-rays from a single X-ray transmitting portion can be formed on the analyzer grating 14. In other words, by superimposing the interference patterns 16a to 16c formed by X-rays from the X-ray transmitting portions 121a to 121c, spatial frequency components specific to the interference patterns 16a to 16c are enhanced. Even when the interference patterns 16a to 16c formed by X-rays from the X-ray transmitting portions 121a to 121c are superimposed while displaced from each other by an integral multiple of the pattern period, it is possible to ensure coincidence between bright portions of the interference patterns 16a to 16c and between dark portions of the interference patterns 16a to 16c. Therefore, the displacement between the interference patterns 16a to 16c may be an integral multiple of the pattern period. The spatial frequency components (i.e., components of a spatial frequency $1/d_{IP}$) specific to the interference patterns 16a to 16c can be considered as being enhanced when the displacement between the interference patterns 16a to 16c is equal to either the pattern period or an integral multiple of the pattern period.

For the interference patterns 16a to 16c formed by X-rays from the X-ray transmitting portions 121a to 121c of the source grating 12 to be superimposed on each other while displaced exactly by the pattern period or an integral multiple of the pattern period, a grating period $d_{0C}$ of the source grating 12 can be defined as follows:

$$d_{0C} = n_1 \times d_{IP} \times \frac{L_{01}}{L_{12}}$$

where $n_1$ is a positive integer, $L_{01}$ is the distance between the source grating 12 and the beam splitter grating 13, and $L_{12}$ is the distance between the beam splitter grating 13 and the analyzer grating 14. Here, the distance between components is the distance between the centers of the components. In the equation, $n_1$ is a value representing the number of pattern periods by which the superimposed interference patterns are displaced from each other. This means that when $n_1=1$, the interference patterns are superimposed while displaced from each other by the pattern period, as in the case of the interference patterns 16a to 16c illustrated in FIG. 4.

Figure 1:
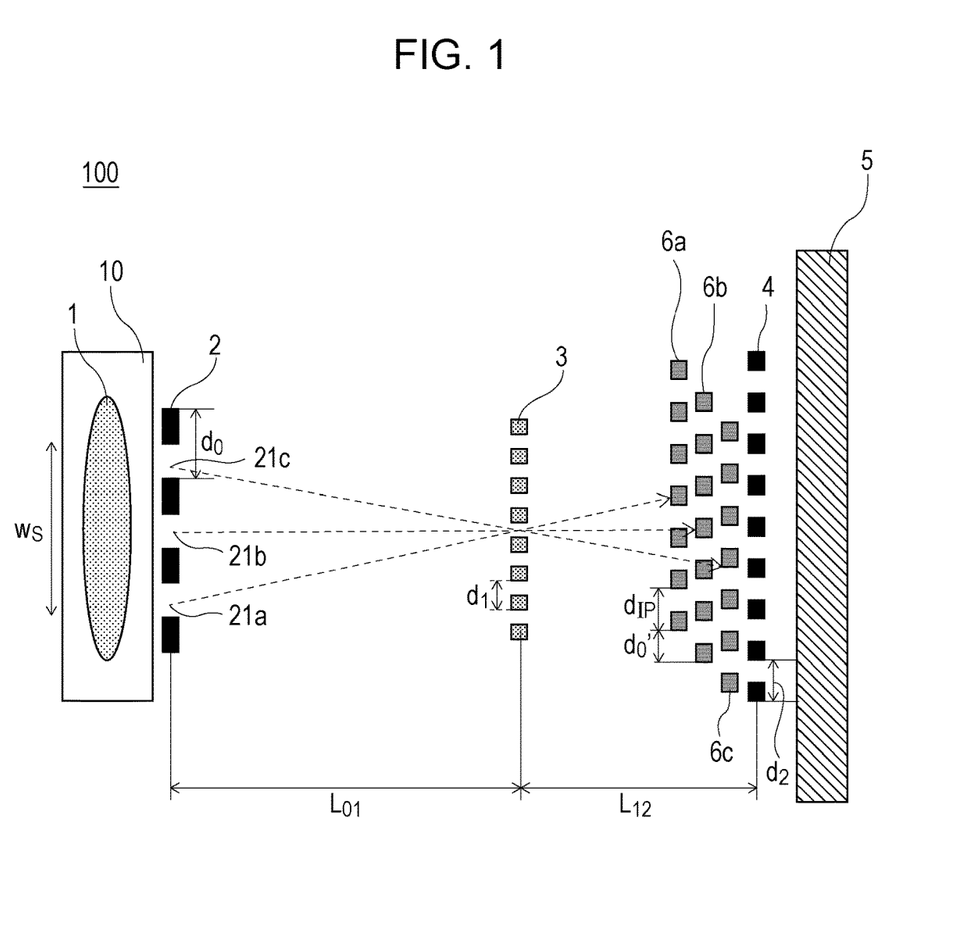
FIG. 1 is a schematic diagram of an X-ray Talbot interferometer according to an embodiment.

On the other hand, in an X-ray Talbot interferometer 100 of the present embodiment, as illustrated in FIG. 1, interference patterns 6a to 6c formed by X-rays from X-ray transmitting portions 21a to 21c of a source grating 2 are superimposed while displaced from each other by a distance, which is different from the interference pattern period $d_{IP}$ in the absence of any object. That is, in the X-ray Talbot interferometer 100 of the present embodiment, the displacement $d_0'$ between the interference patterns 6a to 6c formed by X-rays from the X-ray transmitting portions 21a to 21c is not equal to the interference pattern period $d_{IP}$. Therefore, bright and dark portions of the interference patterns 6a to 6c formed by X-rays from the X-ray transmitting portions 21a to 21c overlap each other without exact coincidence between bright portions and between dark portions. In this case, the grating period $d_0$ of the source grating 2 can be expressed as follows:

$$d_0 = n_1 \times d_{IP} \times \frac{L_{01}}{L_{12}}(1 + \alpha_1) \quad (1)$$

where $\alpha_1$ is a deviation ratio representing the degree of deviation from conditions that allow the interference patterns 6a to 6c to coincide with each other. Note that $\alpha_1$ is not equal to 0 ($\alpha_1 \neq 0$) while it can take a negative value. When $\alpha_1$ is 0, the design conditions of the source grating 2 are the same as those in the comparative example. In the case of $\alpha_1 \neq 0$, superimposing the interference patterns 6a to 6c formed by X-rays from the X-ray transmitting portions 21a to 21c enhances components contained in a sideband resulting from modulation of spatial frequency components specific to the interference patterns 16a to 16c by the presence of the object, instead of enhancing the spatial frequency components specific to the interference patterns 16a to 16c. As described above, a displacement between interference patterns in a typical Talbot-Lau interferometer may be an integral multiple of 2 or more of the pattern period. Similarly, in the Talbot-Lau interferometer of the present embodiment, a displacement between interference patterns may be designed by giving a certain deviation ratio to an integral multiple of 2 or more of the pattern period. However, the design where $n_1$ is an integer of 2 or more is disadvantageous and generally undesirable in that the X-ray transmittance of the entire source grating is lowered. Therefore, the case of $n_1=1$ will be mainly described. Note that $-1/n_1 < \alpha_1 < 1/n_1$ is satisfied.

In FIGS. 1 and 4, for the convenience of explanation, the interference patterns formed by X-rays from the X-ray transmitting portions are shown at different positions in the horizontal direction. However, the interference patterns 6a to 6c are actually formed on the analyzer grating 4 and the interference patterns 16a to 16c are actually formed on the analyzer grating 14. Hence, for example, the distance between the source grating 2 and the interference pattern 6a is equal to the distance between the source grating 2 and the interference pattern 6b.

A general configuration of the X-ray Talbot interferometer according to the present embodiment will now be described. FIG. 1 is a schematic diagram of the X-ray Talbot interferometer 100 according to the present embodiment. The X-ray Talbot interferometer 100 includes the source grating 2 having the X-ray transmitting portions 21a to 21c to transmit some X-rays from an X-ray source 10, and a beam splitter grating 3 configured to diffract the X-rays from the X-ray transmitting portions 21a to 21c of the source grating 2 to form the interference patterns 6a to 6c corresponding to the respective X-ray transmitting portions 21a to 21c. The X-ray Talbot interferometer 100 also includes an analyzer grating 4 configured to block some of the X-rays forming the interference patterns 6a to 6c, and a detector 5 configured to detect the intensity of the X-rays from the analyzer grating 4. The X-ray Talbot interferometer 100 can form an X-ray Talbot interferometer system, together with an object information acquiring unit and an image display unit. The object information acquiring unit may be formed by a computing device including a processor and a storage unit. The object information acquiring unit is capable of recording object information acquired by the detector 5 and outputting the object information to the image display unit. The image display unit may be formed by a display device or a printer.

FIG. 1 illustrates an example where the X-ray source 10 configured to emit X-rays to the source grating 2 forms the X-ray Talbot interferometer 100, together with the three gratings 2, 3, and 4, and the detector 5. Alternatively, the X-ray source 10 may be configured to be separated from, and used in combination with, the X-ray Talbot interferometer 100. In the present invention and the present specification, the term "Talbot interferometer" includes both a Talbot interferometer that includes an X-ray source and a Talbot interferometer that does not include an X-ray source (but may include a space for the X-ray source). Each component of the X-ray Talbot interferometer 100 will now be described.

The X-ray source 10 emits X-rays to the source grating 2. The X-rays to be emitted may be either continuous X-rays or characteristic X-rays. The energy of the X-rays typically ranges from 2 keV to 100 keV. A wavelength selection filter may be provided as appropriate, for example, between the X-ray source 10 and the source grating 2.

Figure 2A:
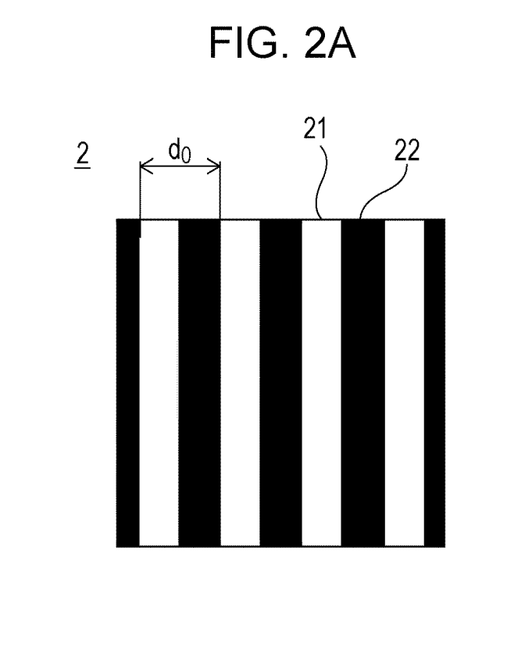
FIGS. 2A to 2C illustrate patterns of gratings according to an embodiment.

FIG. 2A illustrates a grating pattern of the source grating 2. The source grating 2 has a one-dimensional periodic structure where X-ray transmitting portions (which may be referred to as openings) 21 having a high X-ray transmittance and X-ray shielding portions 22 having a low X-ray transmittance are arranged in one direction. The source grating 2 is disposed near X-ray emitting spot 1 of the X-ray source 10 to virtually form an array of linear X-ray-emitting portions (or small X-ray-emitting spots in the case of using a two-dimensional grating).

Figure 2B:
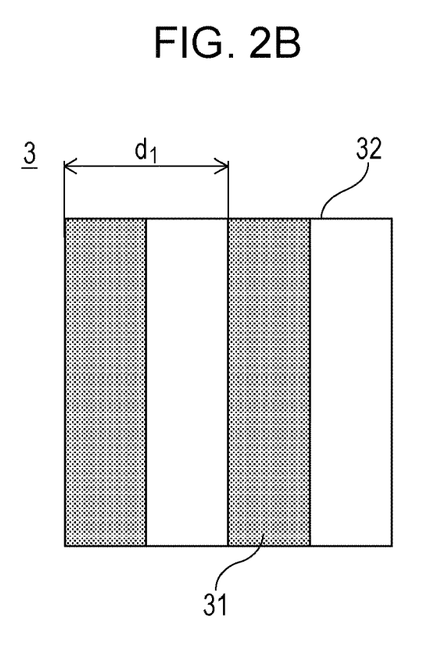

FIG. 2B illustrates a grating pattern of the beam splitter grating 3. The beam splitter grating 3 is a phase-modulation diffraction grating having a one-dimensional periodic structure where phase-advance portions 31 and phase-delay portions 32 are arranged in one direction. The phase-advance portions 31 and the phase-delay portions 32 have a width ratio of 1:1 in the direction of arrangement. The pattern and the amount of phase modulation of the beam splitter grating 3 may be selected from various patterns and values suitable for generally known Talbot interferometers, and are not particularly limited here. Note that the amount of phase modulation refers to a phase difference between X-rays transmitted through the phase-advance portions 31 and the phase-delay portions 32. A beam splitter grating with a phase difference of $\pi$ rad or $\pi/2$ rad is typically used as the beam splitter grating 3, but a beam splitter grating with a phase difference other than that may be used as the beam splitter grating 3. An amplitude-modulation diffraction grating may be used as the beam splitter grating 3 while it has a disadvantage over the phase-modulation diffraction grating in terms of a significant loss of X-rays.

Figure 2C:
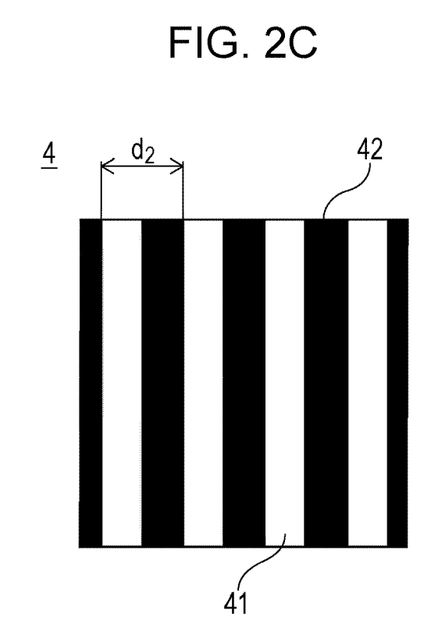

FIG. 2C illustrates a grating pattern of the analyzer grating 4. The analyzer grating 4 has a one-dimensional periodic structure where X-ray transmitting portions 41 having a high X-ray transmittance and X-ray shielding portions 42 having a low X-ray transmittance are arranged in one direction. The X-ray transmitting portions 41 and the X-ray shielding portions 42 have a width ratio of 1:1 in the direction of arrangement.

The grating patterns illustrated in FIGS. 2A to 2C are merely examples, and each grating may have, for example, a two-dimensional periodic structure. The two-dimensional periodic structure may be a square or hexagonal grating structure. The source grating 2 and the analyzer grating 4 having a two-dimensional periodic structure may have either a pattern where isolated X-ray transmitting portions are periodically arranged between X-ray shielding portions, or a pattern where isolated X-ray shielding portions are periodically arranged between X-ray transmitting portions. In the present invention and the present specification, the latter pattern of the shield grating may be referred to as an inverse grating pattern.

The detector 5 may be of any type as long as it is capable of acquiring a two-dimensional X-ray intensity distribution. A line sensor having detection pixels arranged in a line may be used as the detector 5 in the present embodiment. This is because the line sensor can acquire a two-dimensional X-ray intensity distribution by using it in combination with a scanning unit which is capable of scanning in a direction crossing the array direction of the detection pixels. To reduce the time required for imaging, however, it is desirable to use an area sensor having detection pixels arranged in two directions. An imaging plate may be used as the detector 5. The spatial resolution of the detector 5 does not need to be as high as a level that allows detection of the fundamental wave of an interference pattern formed by the beam splitter grating 3. Specifically, the pixel pitch of the detection pixels may be greater than half the period of an interference pattern formed by a virtual linear X-ray-emitting portion. The present embodiment assumes that the pixel pitch of the detection pixels is much greater than the period of the interference pattern.

When no object is placed between the source grating 2 and the analyzer grating 4, the positional relation between a periodic pattern formed by superimposing a plurality of interference patterns and the grating pattern of the analyzer grating 4 is substantially the same over the entire imaging field. Note that the positional relation between the periodic pattern and the grating pattern of the analyzer grating 4 refers to a local positional relation between each of bright and dark portions of the periodic pattern formed on the analyzer grating 4 and the corresponding one of transmitting and shielding portions of the analyzer grating 4 overlapping the bright and dark portions. For example, when both the periodic pattern and the grating pattern of the analyzer grating 4 have a line-and-space pattern, the positional relation between the periodic pattern and the grating pattern of the analyzer grating 4 means whether a bright portion and a shielding portion exactly coincide with each other, whether a bright portion half overlaps a shielding portion, or whether a bright portion and a transmitting portion exactly coincide with each other. In other words, the positional relation between the periodic pattern and the grating pattern of the analyzer grating 4 is the distance between the reference position of each bright portion of the periodic pattern and the reference position of the corresponding shielding portion of the analyzer grating 4. For example, the center of each bright portion in the periodic direction of the periodic pattern is defined as the reference position of the bright portion, and the center of each shielding portion in the periodic direction of the grating pattern is defined as the reference position of the shielding portion. In this case, if the distance between the center of each bright portion and the center of the shielding portion closest to the bright portion in the periodic direction of the periodic pattern is substantially the same over the entire imaging field, the positional relation between the periodic pattern and the grating pattern of the analyzer grating 4 can be considered substantially the same over the entire imaging field. If the periodic pattern and the grating pattern have periods in a plurality of directions, the positional relation between the periodic pattern and the grating pattern of the analyzer grating 4 can be considered substantially the same over the entire imaging field when the distance between the reference positions in each periodic direction is substantially the same. In the present invention and the present specification, "distance is substantially the same" means that the difference between maximum and minimum values of the distance between the reference position of each bright portion and the reference position of the shielding portion closest to the bright portion is $d_{IP}/4$ or less. Also, "positional relation between the periodic pattern and the grating pattern is substantially the same over the entire imaging field" means that the distance between reference positions is substantially the same. It is preferable that the difference between maximum and minimum values of the distance between the reference position of each bright portion and the reference position of the shielding portion closest to the bright portion be $d_{IP}/8$ or less. To make the positional relation between the periodic pattern and the grating pattern the same over the entire imaging field, it is only necessary that the interference patterns forming the periodic pattern and the analyzer grating 4 be the same in pitch and periodic direction. The ranges of allowable differences in pitch and periodic direction vary in accordance with the pitch and the size of the imaging field.

An X-ray intensity distribution formed on the detector 5 is uniform. In the present invention and the present specification, "X-ray intensity distribution formed on the detector 5 is uniform" means that the intensity of X-rays incident on the detection surface of the detector 5 is substantially the same over the entire imaging field in the detection surface. The imaging field refers to a region obtained by projecting the imaging range of the object onto the detection surface. The imaging field typically coincides with the entire detection surface, but only part of the detection surface may serve as the imaging field.

As in the case of the X-ray Talbot-Lau interferometer 1100 of the related art, the distance $L_{01}$ between the source grating 2 and the beam splitter grating 3 and the distance $L_{12}$ between the beam splitter grating 3 and the analyzer grating 4 may be designed such that the visibility of interference patterns is particularly high on the analyzer grating 4. Here, the design takes into account the Talbot effect produced when X-rays from each of virtual linear X-ray-emitting portions formed by the source grating 2 are diffracted by the beam splitter grating 3.

By using a simple model, the following describes the effect of the present embodiment where the interference patterns formed by X-rays from the virtual linear X-ray-emitting portions are superimposed while displaced from each other by an amount not equal to the pattern period, and also describes the resulting image produced using the dark-field technique or intermediate technique.

First, a coordinate system (x, y) is defined on the analyzer grating 4. The periodic direction of the interference patterns coincides with the x-axis direction. An intensity distribution $g_{IPo}(x, y)$ of an interference pattern on the analyzer grating 4 formed by X-rays emitted from a single point on the source grating 2 can be written as follows:

$$g_{IPo}(x, y) = a(x, y) + b(x, y)\cos\left[\frac{2\pi}{d_{IP}}x + \phi(x, y)\right] \quad (2)$$

where $a(x, y)$ is the average intensity distribution of the interference pattern reflecting the X-ray transmittance distribution of the object, $b(x, y)$ is the amplitude distribution of the interference pattern reflecting the X-ray transmittance distribution of the object and the X-ray small-angle scattering power distribution of the object with respect to the periodic direction of the interference pattern, and $\phi(x, y)$ is the phase distribution of the interference pattern reflecting a distribution obtained by differentiating, along the periodic direction of the interference pattern, the phase distribution of X-rays transmitted through the object. Note that the X-ray small-angle scattering power distribution of the object refers to the spatial distribution of power of small-angle scattering caused by microparticles and fine fibers in the object, edges in structures, and the like. Also, the distribution obtained by differentiating, in a certain direction, the phase distribution of X-rays transmitted through the object refers to the distribution of deflection angles of X-rays refracted by the object in the direction of differentiation described above. In the present invention and the present specification, information about the X-ray transmittance distribution of the object may be referred to as absorption information, information about the differential phase distribution of X-rays transmitted through the object may be referred to as differential phase information, and information about the X-ray small-angle scattering power distribution of the object may be referred to as scattering information. The phase distribution and the differential phase distribution of X-rays transmitted through the object, and a secondary differential phase distribution obtained by differentiating the differential phase distribution in the same direction may be collectively referred to as phase information of the object.

Here, the spatial frequency components specific to the interference patterns in the present embodiment are spatial frequency components having a periodic direction in the x-axis direction and a spatial frequency of $1/d_{IP}$. The spatial frequency components specific to the interference patterns can be considered as being amplitude-modulated and phase-modulated by $b(x, y)$ and $\phi(x, y)$ representing the object information. In the present specification, the spatial frequency components specific to interference patterns and modulated by object information may be referred to as a carrier wave. Harmonic components, instead of fundamental wave components, of the interference patterns may be used as a carrier wave. However, harmonic components of the interference patterns are generally very small as compared to fundamental wave components, and thus are rarely used as a carrier wave. By using the following equation $$c(x,y)=b(x,y)e^{i\phi(x,y)} \quad (3),$$

equation (2) can be rewritten as follows:

$$g_{IPo}(x, y) = a(x, y) + \frac{1}{2}c(x, y)e^{i\frac{2\pi}{d_{IP}}x} + \frac{1}{2}c^*(x, y)e^{-i\frac{2\pi}{d_{IP}}x} \quad (4)$$

where * represents a complex conjugate. Computing the two-dimensional Fourier transform of both sides leads to the following equation:

$$G_{IPo}(\xi, \eta) = A(\xi, \eta) + \frac{1}{2}C\left(\xi - \frac{1}{d_{IP}}, \eta\right) + \frac{1}{2}C^*\left(\xi + \frac{1}{d_{IP}}, \eta\right) \quad (5)$$

where each capital letter represents the Fourier transform of the corresponding function (the same applies to the following equations), $\xi$ represents a spatial frequency in the x-axis direction, and $\eta$ represents a spatial frequency in the y-axis direction.

The X-ray intensity distribution on the analyzer grating 4 will be discussed, which takes into account the presence of the X-ray emitting spot 1 having a spatial spread and the source grating 2. The object and the beam splitter grating 3 are approximated to be at the same position. The X-ray emitting spot 1 and the source grating 2 are also approximated to be at the same position.

With respect to the position coordinates $(x_0, y_0)$ in the x-axis and y-axis directions at the position of the X-ray emitting spot 1 and the source grating 2, a function representing the shape of the emission intensity distribution of the X-ray emitting spot 1 is expressed as $g_S(x_0, y_0)$. The transmittance distribution of the source grating 2 is expressed as $t_0(x_0, y_0)$. In this case, the effective emission intensity distribution $g_{S0}(x_0, y_0)$ of the X-ray emitting spot 1 can be expressed as follows:

$$g_{S0}(x_0,y_0) = g_S(x_0,y_0) t_0(x_0,y_0) \quad (6).$$

Additionally, the X-ray intensity distribution $g_{IP}(x, y)$ on the analyzer grating 4 can be approximately expressed as a convolution of $g_{IPo}(x, y)$ and a point spread function $h_{S0}(x, y)$ representing blurring caused by the effective emission intensity distribution of the X-ray emitting spot 1, as follows:

$$g_{IP}(x,y) = g_{IPo}(x,y) * h_{S0}(x,y) \quad (7)$$

where * represents a convolution. Note that $g_{IP}(x, y)$ differs from $g_{IPo}(x, y)$ in that it represents the intensity distribution of interference patterns actually formed on the analyzer grating 4 (i.e., interference patterns formed by all X-rays transmitted through the source grating 2). Also, $g_{IP}(x, y)$ can be considered as representing the intensity distribution of a periodic pattern formed by superimposing a plurality of interference patterns produced by X-rays from the X-ray transmitting portions 21a to 21c of the source grating 2. Additionally, $h_{S0}(x, y)$ can be written as follows:

$$h_{S0}(x, y) \propto g_{S0}\left(-\frac{L_{01}}{L_{12}}X, -\frac{L_{01}}{L_{12}}y\right). \quad (8)$$

Here, $h_S(x, y)$ is a function that can be expressed as follows:

$$h_S(x, y) \propto g_S\left(-\frac{L_{01}}{L_{12}}X, -\frac{L_{01}}{L_{12}}y\right). \quad (9)$$

Note that $h_S(x, y)$ is a point spread function in the absence of the source grating 2. If the source grating 2 has a simple sinusoidal transmittance distribution, $t_0(x_0, y_0)$ can be written as follows by ignoring absolute values:

$$t_0(x_0, y_0) = 1 + \cos\left(\frac{2\pi}{d_0}x_0\right). \quad (10)$$

A relative displacement $d_0'$ between interference patterns can be written as follows using the pitch $d_0$ of the source grating 2 and the geometry $(L_{12}, L_{01})$ of the X-ray Talbot interferometer 100:

$$d_0' = d_0 \frac{L_{12}}{L_{01}}. \quad (11)$$

In this case, $h_{S0}(x, y)$ can be written as follows:

$$h_{S0}(x, y) = h_S(x, y)\left[1 + \cos\left(\frac{2\pi}{d_0'}x\right)\right]. \quad (12)$$

Then, $H_{S0}(\xi, \eta)$, which is the Fourier transform of $h_{S0}(x, y)$, can be expressed as follows:

$$H_{S0}(\xi, \eta) = H_S(\xi, \eta) + \frac{1}{2}H_S\left(\xi - \frac{1}{d_0'}, \eta\right) + \frac{1}{2}H_S\left(\xi + \frac{1}{d_0'}, \eta\right). \quad (13)$$

Thus, $G_{IP}(\xi, \eta)$, which is the Fourier transform of $g_{IP}(x, y)$, can be written as follows using equations (5), (7), and (13) and the convolution theorem:

$$G_{IP}(\xi, \eta) = G_{IPo}(\xi, \eta) H_{S0}(\xi, \eta) \approx A(\xi, \eta) H_S(\xi, \eta) + \quad (14)$$
$$\frac{1}{4}C\left(\xi - \frac{1}{d_{IP}}, \eta\right) H_S\left(\xi - \frac{1}{d_0'}, \eta\right) + \frac{1}{4}C^*\left(\xi + \frac{1}{d_{IP}}, \eta\right) H_S\left(\xi + \frac{1}{d_0'}, \eta\right).$$

Here, the spatial changes of $a(x, y)$, $b(x, y)$, $\phi(x, y)$, and $h_S(x, y)$ are assumed to be much slower than $d_{IP}$ and $d_0'$.

As can be seen from equation (14), $c(x, y)$ is filtered by a frequency filter $H_S$ in the process of information transmission, through the effect of the X-ray emitting spot 1 having a spatial spread and the source grating 2. As shown in equation (3), $c(x, y)$ has information about the amplitude distribution of the interference pattern and the phase distribution of the interference pattern, and thus has absorption information, phase information, and scattering information of the object. Therefore, equation (14) indicates that the object information is filtered by the frequency filter $H_S$. Also, the shape of the frequency filter $H_S$ is found to be determined by the emission intensity distribution of the X-ray emitting spot 1 and $L_{01}$ and $L_{12}$, and the position of the frequency filter $H_S$ relative to $C(\xi, \eta)$ is found to be determined by the period $d_{IP}$ of the interference patterns, the grating period $d_0$ of the source grating 2, and $L_{01}$ and $L_{12}$.

Figure 3A:
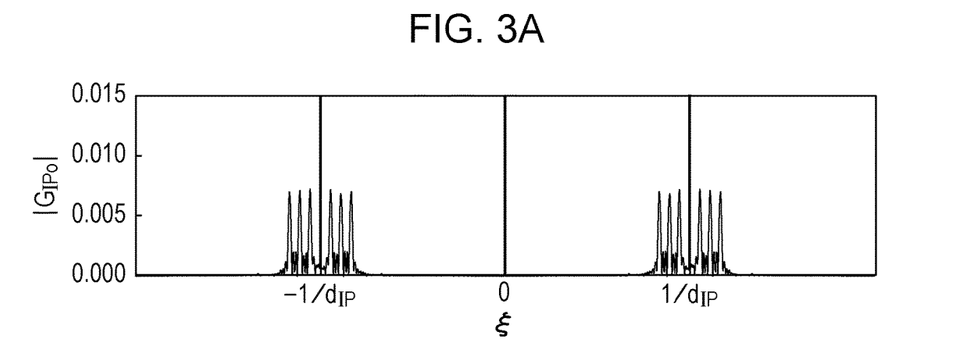
FIGS. 3A to 3C illustrate changes in the spatial frequency spectrum of an interference pattern formed on an analyzer grating according to an embodiment.
Figure 3B:
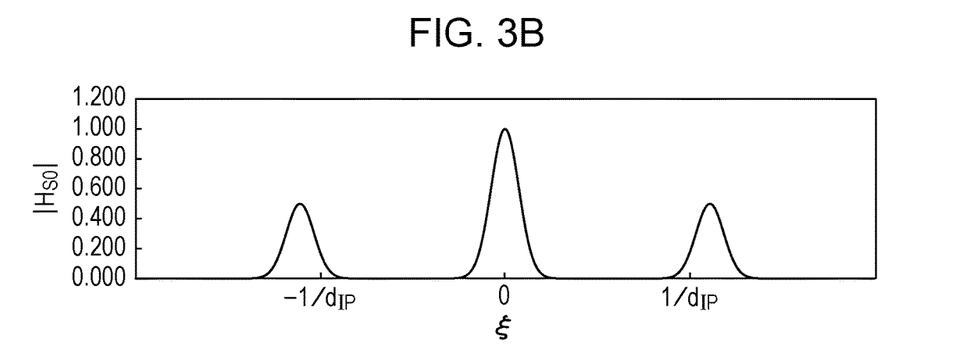
Figure 3C:
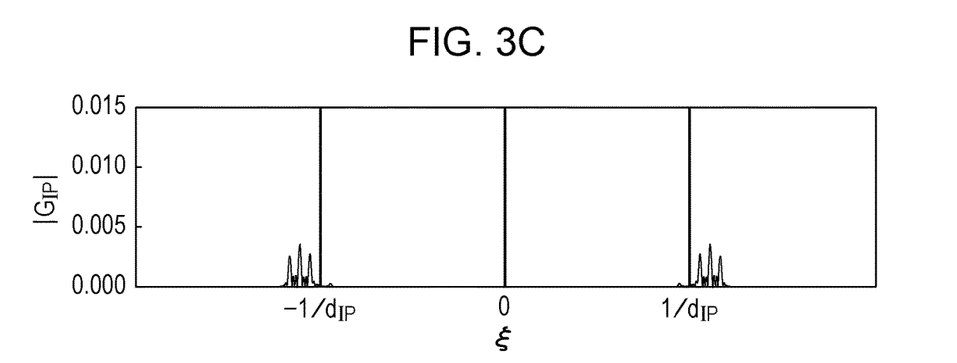

FIGS. 3A to 3C illustrate changes in the spatial frequency spectrum of an interference pattern formed on the analyzer grating 4, and show a process in which $G_{IPo}(\xi, \eta)$ is converted to $G_{IP}(\xi, \eta)$ by being filtered by $H_{S0}(\xi, \eta)$ as in equation (14). Note that FIGS. 3A to 3C each show the profile of each spectrum on the $\xi$-axis. Also, $a(x, y)$ and $b(x, y)$ are assumed to be constants (i.e., independent of x and y), shape information of the object is assumed to be reflected in $\phi(x, y)$, and $h_S(x, y)$ is assumed to have a two-dimensional Gaussian shape. FIGS. 3A, 3B, and 3C show $|G_{IPo}(\xi, \eta)|$, $|H_{S0}(\xi, \eta)|$, and $|G_{IP}(\xi, \eta)|$, respectively.

A spectrum around $\xi = 1/d_{IP}$ in FIG. 3A corresponds to components of $(1/2)C(\xi - 1/d_{IP}, \eta)$, and a spectrum around $\xi = -1/d_{IP}$ in FIG. 3A corresponds to components of $(1/2)C^*(\xi + 1/d_{IP}, \eta)$. A spectrum around $\xi = 1/d_{IP}$ in FIG. 3B corresponds to components of $(1/2)H_S(\xi - 1/d_0', \eta)$, and a spectrum around $\xi = -1/d_{IP}$ in FIG. 3B corresponds to components of $(1/2)H_S(\xi + 1/d_0', \eta)$. This example assumes a case where $d_0'$ is slightly smaller than $d_{IP}$. Therefore, the center of the filter applied around the carrier wave is located slightly to the high-frequency side of the carrier wave. FIG. 3C shows a spectrum obtained after filtering with $H_{S0}(\xi, \eta)$. In this example, the sideband structure is originally highly symmetric with respect to the carrier wave. However, by the effect of applying an asymmetric filter to the carrier wave, the original sideband structure is transformed into a less symmetric sideband structure as shown.

Next, an X-ray intensity distribution will be discussed, which is eventually measured by transmitting X-rays through the analyzer grating 4 and allowing the X-rays to enter the detector 5. A transmittance distribution $t_2(x, y)$ of the analyzer grating 4 can be expressed as follows by ignoring absolute values:

$$t_2(x, y) = 1 + \cos\left(\frac{2\pi}{d_2}x - \phi_r\right) \tag{15}$$

where $d_2$ is the grating period of the analyzer grating 4, and $\phi_r$ is the phase of the analyzer grating 4 (corresponding to the position of the analyzer grating 4 in the x-axis direction) and is in the range of $0 \leq \phi_r < 2\pi$. When $\phi_r=0$, the bright portions of the interference patterns formed at the position of the analyzer grating 4 coincide with the transmitting portions of the analyzer grating 4 in the area free from the effect of the object. On the other hand, when $\phi_r=\pi$, the bright portions of the interference patterns formed at the position of the analyzer grating 4 coincide with the shielding portions of the analyzer grating 4 in the area free from the effect of the object. That is, imaging performed with $\phi_r=0$ is the bright-field technique, and imaging performed with $\phi_r=\pi$ is the dark-field technique. When the bright portions of the interference patterns formed at the position of the analyzer grating 4 coincide with the transmitting portions of the analyzer grating 4, the distance between the center of each bright portion and the center of the corresponding transmitting portion is 0 in the periodic direction (x-axis direction here) of the interference patterns. Similarly, when the bright portions of the interference patterns formed at the position of the analyzer grating 4 coincide with the shielding portions of the analyzer grating 4, the distance between the center of each bright portion and the center of the corresponding shielding portion is 0 in the periodic direction of the interference patterns. In the case of performing the bright-field technique, the distance between the center of each bright portion and the center of the corresponding transmitting portion may be 0 ($\phi_r=0$). However, even when the interference patterns and the analyzer grating 4 are slightly displaced from each other, an X-ray intensity distribution having the same characteristics as the X-ray intensity distribution obtained by the bright-field technique can be obtained. The same applies to the case of performing the dark-field technique. Therefore, in the present invention and the present specification, imaging performed when the distance between the center of each bright portion and the center of the corresponding transmitting portion is less than or equal to ⅛ times the period ($0 \leq \phi_r \leq \pi/4$ or $7\pi/4 \leq \phi_r < 2\pi$) is considered as the bright-field technique. On the other hand, imaging performed when the distance between the center of each bright portion and the center of the corresponding shielding portion is less than or equal to ⅛ times the period ($3\pi/4 \leq \phi_r \leq 5\pi/4$) is considered as the dark-field technique. It is preferable that the distance between the center of each bright portion and the center of the corresponding transmitting portion be less than or equal to 1/10 times the period ($0 \leq \phi_r \leq \pi/5$ or $9\pi/5 \leq \phi_r < 2\pi$), or the distance between the center of each bright portion and the center of the corresponding shielding portion be less than or equal to 1/10 times the period ($4\pi/5 \leq \phi_r \leq 6\pi/5$). This is because the characteristics of the bright-field technique or the dark-field technique are particularly reflected in the X-ray intensity distribution.

When $\phi_r=\pi/2$ or $\phi_r=3\pi/2$, the distance between the center of each bright portion and the center of the corresponding transmitting portion, and the distance between the center of each bright portion and the center of the corresponding shielding portion, are both ¼ times the pitch of the interference patterns. In this case, the intensity of X-rays transmitted through the analyzer grating 4 is the average of the maximum value (X-ray intensity when $\phi_r=0$) and the minimum value (X-ray intensity when $\phi_r=\pi$). When the interference patterns and the analyzer grating 4 have this positional relation, the characteristics of an X-ray intensity distribution obtained by the intermediate technique are most strongly reflected. However, even when the interference patterns and the analyzer grating 4 are slightly displaced from each other, an X-ray intensity distribution having the same characteristics as the X-ray intensity distribution obtained by the intermediate technique can be obtained. Therefore, in the present invention and the present specification, imaging performed when the distance between the center of each bright portion and the center of the corresponding transmitting portion is greater than ⅛ times the period, and the distance between the center of each bright portion and the center of the corresponding shielding portion is greater than ⅛ times the period ($\pi/4 < \phi_r < 3\pi/4$ or $5\pi/4 < \phi_r < 7\pi/4$) is considered as the intermediate technique.

As in the case of the source grating 2, the grating period $d_2$ of the analyzer grating 4 may be an integral multiple of 2 or more of $d_{IP}$ or a value close thereto. However, again this is generally undesirable in that the X-ray transmittance is lowered. Therefore, the following describes the case where $d_2$ has a value close to $d_{IP}$. Since the analyzer grating 4 is normally disposed very close to the detection surface of the detector 5, the analyzer grating 4 and the detection surface are approximated to be at the same position. Here, the intensity distribution of X-rays transmitted through the analyzer grating 4 coincides with the X-ray intensity distribution formed on the detection surface. A point spread function (PSF) specific to intensity distribution measurement made by the detector 5 used is represented by $h_D(x, y)$. In this case, the X-ray intensity distribution $g_M(x, y)$ eventually measured can be written as follows using the intensity distribution of X-rays transmitted through the analyzer grating 4 ($g_{IP}(x, y)t_2(x, y)$) and the point spread function of the detector 5:

$$g_M(x,y) = [g_{IP}(x,y)t_2(x,y)] * h_D(x,y) \tag{16}$$

Therefore, $G_M(\xi, \eta)$, which is the Fourier transform of $g_M(x, y)$, can be written as follows:

$$G_M(\xi, \eta) = [G_{IP}(\xi, \eta) * T_2(\xi, \eta)]H_D(\xi, \eta) \approx \left[A(\xi, \eta)H_S(\xi, \eta) + \frac{1}{8}C\left(\xi - \frac{1}{d_{IP}} + \frac{1}{d_2}, \eta\right)H_S\left(\xi - \frac{1}{d_0'} + \frac{1}{d_2}, \eta\right)e^{i\phi_r} + \frac{1}{8}C^*\left(\xi + \frac{1}{d_{IP}} - \frac{1}{d_2}, \eta\right)H_S\left(\xi + \frac{1}{d_0'} - \frac{1}{d_2}, \eta\right)e^{-i\phi_r}\right]H_D(\xi, \eta). \tag{17}$$

Here, terms located in a region far away from the origin in the ($\xi$, $\eta$) space are ignored on the assumption that their values are made sufficiently small by filtering with $H_D(\xi, \eta)$. Also, $|H_D(\xi, \eta)|$ is a function corresponding to a modulation transfer function (MTF) of the detector 5.

Since $d_2=d_{IP}$ is satisfied in the present embodiment, equation (17) can be rewritten as follows:

$$G_M(\xi, \eta) \approx \left[A(\xi, \eta)H_S(\xi, \eta) + \frac{1}{8}C(\xi, \eta)H_S(\xi - \xi_0, \eta)e^{i\phi_r} + \right. \tag{18}$$

-continued
$$\frac{1}{8}C^*(\xi, \eta)H_S(\xi+\xi_0, \eta)e^{-i\phi_r}\bigg]H_D(\xi, \eta)$$

where $\xi_0=1/d_0'-1/d_{IP}$.

To simplify the discussion, $h_S(x, y)$ is assumed to be an even function. Since $h_S(x, y)$ is a real function at the same time, $H_S(\xi, \eta)$, which is the Fourier transform of $h_S(x, y)$, is also a real even function. $H_S(\xi, \eta)$ may have a structure with a plurality of extremal values depending on the shape of $h_S(x, y)$. In this case, the value of $\xi_0$ is assumed to be small enough to be contained in the main lobe at the origin in $H_S(\xi, \eta)$. Then, when $H_S(\xi-\xi_0, \eta)$ and $H_S(\xi+\xi_0, \eta)$ are each Taylor-expanded around $(\xi, \eta)=(0, 0)$, and terms related to $\eta$ and the second and higher order terms of $\xi$ are ignored, $G_M(\xi, \eta)$ can be approximately written as follows:

$$G_M(\xi, \eta) \approx \qquad (19)$$
$$\left\{A(\xi, \eta)H_S(\xi, \eta) + \frac{1}{8}C(\xi, \eta)\left[H_S(-\xi_0, 0) + \left(\frac{\partial H_S}{\partial \xi}\right)(-\xi_0, 0)\xi\right]e^{i\phi_r} + \right.$$
$$\left. \frac{1}{8}C^*(\xi, \eta)\left[H_S(\xi_0, 0) + \left(\frac{\partial H_S}{\partial \xi}\right)(\xi_0, 0)\xi\right]e^{-i\phi_r}\right\}H_D(\xi, \eta) =$$
$$\left\{A(\xi, \eta)H_S(\xi, \eta) + \frac{1}{8}C(\xi, \eta)\left[H_S(-\xi_0, 0) + \left(\frac{\partial H_S}{\partial \xi}\right)(-\xi_0, 0)\xi\right]e^{i\phi_r} + \right.$$
$$\left. \frac{1}{8}C^*(\xi, \eta)\left[H_S(-\xi_0, 0) - \left(\frac{\partial H_S}{\partial \xi}\right)(-\xi_0, 0)\xi\right]e^{-i\phi_r}\right\}H_D(\xi, \eta) =$$
$$\left\{A(\xi, \eta)H_S(\xi, \eta) + \frac{1}{8}H_S(-\xi_0, 0)[C(\xi, \eta)e^{i\phi_r} + C^*(\xi, \eta)e^{-i\phi_r}] + \right.$$
$$\left. \frac{1}{8}\left(\frac{\partial H_S}{\partial \xi}\right)(-\xi_0, 0)\xi[C(\xi, \eta)e^{i\phi_r} - C^*(\xi, \eta)e^{-i\phi_r}]\right\}H_D(\xi, \eta).$$

Therefore, $g_M(x, y)$ can be approximately written as follows:

$$g_M(x, y) \approx a(x, y) * h_S(x, y) * h_D(x, y) + \qquad (20)$$
$$\frac{1}{8}H_S(-\xi_0, 0)[c(x, y)e^{i\phi_r} + c^*(x, y)e^{-i\phi_r}] * h_D(x, y) + \frac{1}{8}\left(\frac{\partial H_S}{\partial \xi}\right)$$
$$(-\xi_0, 0)\left[e^{i\phi_r}\frac{1}{2\pi i}\frac{\partial c(x, y)}{\partial x} - e^{-i\phi_r}\frac{1}{2\pi i}\frac{\partial c^*(x, y)}{\partial x}\right] * h_D(x, y) =$$
$$a(x, y) * h_S(x, y) * h_D(x, y) + \frac{1}{4}H_S(-\xi_0, 0)b(x, y)$$
$$\cos[\phi(x, y) + \phi_r] * h_D(x, y) + \frac{1}{16\pi}\left(\frac{\partial H_S}{\partial \xi}\right)(-\xi_0, 0) \times$$
$$\left\{\frac{e^{i\phi_r}}{i}\left[\frac{\partial b(x, y)}{\partial x}e^{i\phi(x,y)} + ib(x, y)\frac{\partial \phi(x, y)}{\partial x}e^{i\phi(x,y)}\right] - \right.$$
$$\left. \frac{e^{-i\phi_r}}{i}\left[\frac{\partial b(x, y)}{\partial x}e^{-i\phi(x,y)} - ib(x, y)\frac{\partial \phi(x, y)}{\partial x}e^{-i\phi(x,y)}\right]\right\} *$$
$$h_D(x, y) = a(x, y) * h_S(x, y) * h_D(x, y) +$$
$$\frac{1}{4}H_S(-\xi_0, 0)b(x, y)\cos[\phi(x, y) + \phi_r] * h_D(x, y) +$$
$$\frac{1}{8\pi}\left(\frac{\partial H_S}{\partial \xi}\right)(-\xi_0, 0) \times \left\{\frac{\partial b(x, y)}{\partial x}\sin[\phi(x, y) + \phi_r] + \right.$$
$$\left. b(x, y)\frac{\partial \phi(x, y)}{\partial x}\cos[\phi(x, y) + \phi_r]\right\} * h_D(x, y).$$

On the rightmost side of equation (20), the first term represents a contrast which is based on the absorption information of the object and remains after elimination of the effect of interference fringes. The second term on the rightmost side of equation (20) represents part of the effects of amplitude modulation b(x, y) and phase modulation φ(x, y) of the interference fringes. For example, the second term indicates that, in the case when $\phi_r=\pi/2$, in other words, in the case of a condition corresponding to imaging performed using the intermediate technique described above, the effect of φ(x, y) reflecting the differential phase information of the object is strongly reflected in the image. The second term also indicates that, in the case when $\phi_r=\pi$, in other words, in the case of a condition corresponding to imaging performed using the dark-field technique described above, although the effect of φ(x, y) is not much reflected in the image unless the value of φ(x, y) is large enough, the effect of b(x, y) containing the scattering information of the object is strongly reflected in the image. Note that the second term is a term which maximizes its variation when $\xi_0=0$, and shows the same characteristics as the Talbot interferometer of the related art in terms of how the effects of b(x, y) and φ(x, y) are reflected in the image. On the other hand, the third term on the rightmost side of equation (20) is a term that can have a non-zero value only when $\xi_0 \neq 0$, that is, when the displacement $d_0'$ between interference patterns is not equal to ($\neq$) the pattern pitch $d_{IP}$ of the interference patterns. The third term thus represents the unique effects of the present embodiment. The first term within braces ({ }) in the third term on the rightmost side of equation (20), $$\frac{\partial b(x, y)}{\partial x}\sin[\phi(x, y) + \phi_r],$$

mainly represents the effect of a differential value of b(x, y) along the x-axis direction. The differential value of b(x, y) reflects a differential value of absorption information (differential absorption information) and a differential value of scattering information (differential scattering information). The absolute value of sin [φ(x, y)+$\phi_r$] is large when imaging is performed using the intermediate technique (where $\phi_r$ takes a value close to π/2 or 3π/2), and hence this term indicates that the differential absorption information and the differential scattering information have significant effects on the image in the case of imaging using the intermediate technique. On the other hand, when imaging is performed using the dark-field technique (where $\phi_r$ takes a value close to π), this term generally has no significant effect on the image.

The second term within braces ({ }) in the third term on the rightmost side of equation (20), $$b(x, y)\frac{\partial \phi(x, y)}{\partial x}\cos[\phi(x, y) + \phi_r],$$

mainly represents the effects of b(x, y) and differential value of φ(x, y) along the x-axis direction. The differential value of φ(x, y) reflects a differential value of differential phase information of the object (secondary differential phase information or wavefront curvature). The absolute value of cos [φ(x, y)+$\phi_r$] is large when imaging is performed using the dark-field technique, and hence this term indicates that the secondary differential phase information has a significant effect on the image in the case of imaging using the dark-field technique. On the other hand, when imaging is performed using the intermediate technique, this term generally has no significant effect on the image. Thus, the third term on the rightmost side of equation (20) represents the effect of causing scattering information to be strongly reflected in the X-ray intensity distribution on the detector 5, in the case of using the intermediate technique which is originally unable to acquire scattering information. The third term on the rightmost side of equation (20) also represents the effect of causing phase information to be significantly reflected in the X-ray intensity distribution on the detector 5, in the case of using the dark-field technique which originally has low sensitivity to phase information.

The greater the derivative of $H_S(\xi, \eta)$ at $\xi=-\xi_0$, the greater the effect the third term generally has on the image.

In summary, when imaging using the intermediate technique is performed with the interferometer of the present embodiment, an image which strongly reflects absorption information, differential phase information, differential absorption information, and differential scattering information can be acquired. When imaging using the dark-field technique is performed with the interferometer of the present embodiment, an image which strongly reflects absorption information, scattering information, and secondary differential phase information can be acquired.

In the case of using the bright-field technique, since cos$[\phi(x, y)+\phi_r]$, which is the second term within braces ({ }) in the third term on the rightmost side of equation (20), has a large value, an X-ray intensity distribution which more strongly reflects phase information than the related art can be formed on the detector 5, as in the case of using the dark-field technique.

As described above, absorption information, phase information, and scattering information of the object can be acquired in the present embodiment. Even when the dark-field technique or bright-field technique is performed using the Talbot interferometer of the present embodiment, phase information is strongly reflected in the acquired X-ray intensity distribution by adding the third term described above. It is thus possible to acquire phase information with higher sensitivity than the dark-field technique of the related art.

Other features of the present embodiment and imaging techniques will now be described.

In imaging using the dark-field technique, the level of X-ray shot noise is generally low, because the X-ray intensity in the background of the image is relatively low. Therefore, in imaging using the dark-field technique, scattering information and secondary differential phase information can be acquired with a relatively high signal-to-noise (S/N) ratio.

In imaging using the bright-field technique, the amount of X-rays lost by transmission through the analyzer grating 4 is small. Therefore, in imaging using the bright-field technique, it is possible not only to acquire absorption information with a relatively high S/N ratio, but also to acquire scattering information and secondary differential phase information.

In the case of using the dark-field technique or bright-field technique, changes in the X-ray intensity in the background resulting from changes in the relative position of gratings are smaller than in the case of using the intermediate technique, and hence the requirement for accuracy in the alignment of gratings is lower.

In the present embodiment, the frequency filter $H_S$ can be applied to the spectrum of each of $C(\xi, \eta)$ and $C^*(\xi, \eta)$ reflecting the object information, at a position off the center of the spectrum. This allows components in the high-frequency region in c(x, y) to remain more easily, and thus can improve the spatial resolution of imaging.

As described above, the gratings used in the interferometer may have a two-dimensional grating pattern, such as a square grating pattern or a hexagonal grating pattern. This is advantageous in that, in the case of using the dark-field technique or bright-field technique, scattering information for a plurality of directions and secondary differential phase information along a plurality of directions can be acquired at the same time. In the case of using the intermediate technique of the related art, differential phase information of the object for one direction can be acquired with high sensitivity. However, even when gratings with a two-dimensional grating pattern are used, differential phase information for a plurality of directions cannot be acquired at the same time. When the dark-field technique is performed in the present embodiment, either one of the source grating 2 and the analyzer grating 4 may have the inverse grating pattern described above.

The range of $\xi_0$ for achieving particularly high imaging performance in the interferometer of the present embodiment will now be described.

When the X-ray emitting spot 1 is assumed to have a two-dimensional Gaussian emission intensity distribution, $g_S(x_0, y_0)$ can be written as follows:

$$g_S(x_0, y_0) = e^{-\frac{x_0^2+y_0^2}{2\sigma_S^2}} \quad (21)$$

where $\sigma_S$ is a constant that determines the size of spatial spread of the X-ray emitting spot 1. In this case, $h_S(x, y)$ can be written as follows from equation (9):

$$h_S(x, y) \propto e^{-\frac{x^2+y^2}{2\sigma_S'^2}} \quad (22)$$

where $\sigma_S'$ is as follows:

$$\sigma_S' = \sigma_S \frac{L_{12}}{L_{01}}. \quad (23)$$

In this case, $H_S(\xi, \eta)$, which is the Fourier transform of $h_S(x, y)$, can be expressed as follows by ignoring coefficients:

$$H_S(\xi, \eta) = e^{-\frac{\xi^2+\eta^2}{2\sigma_{SF}^2}}. \quad (24)$$

This also has a Gaussian shape. Note however that $\sigma_{SF}$ is a constant that determines the width of $H_S(\xi, \eta)$ and can be expressed as follows:

$$\sigma_{SF} = \frac{1}{2\pi\sigma_S'} = \frac{1}{2\pi\sigma_S}\frac{L_{01}}{L_{12}}. \quad (25)$$

When $n_1=1$, $\xi_0$ can be written as follows:

$$\xi_0 = \frac{1}{d_0'} - \frac{1}{d_{IP}} = -\frac{1}{d_{IP}}\frac{\alpha_1}{1+\alpha_1} \approx -\frac{\alpha_1}{d_{IP}}. \quad (26)$$

Note that $|\alpha_1| \ll 1$. $C(\xi-1/d_{IP}, \eta)$, which is the spectrum of object information, is two-dimensionally distributed around the carrier wave at the center. As described above, $\phi(x, y)$ reflects a distribution obtained by differentiating, in the direction of the carrier wave, the phase distribution of X-rays transmitted through the object. In this case, the components of $C(\xi-1/d_{IP}, \eta)$ strongly appear particularly in the $\xi$-axis direction, which is the direction of the carrier wave. Therefore, the frequency filter $H_S$ may be shifted along the $\xi$-axis ($\xi_0 \neq 0$). If $|\xi_0|$ has a large value, many higher-frequency components in $c(x, y)$ can be transmitted. At the same time, however, this is disadvantageous in that the total amount of signals is reduced due to loss of low-frequency components. To effectively achieve the advantages of the present embodiment while preventing such loss of low-frequency components, $\xi_0$ may be selected to satisfy the following:

$$0.3\sigma_{SF} < |\xi_0| < 3.0\sigma_{SF} \qquad (27).$$

If the value of $|\xi_0|$ is around $0.3\sigma_{SF}$, the interferometer can have the unique features of the present embodiment while having imaging performance relatively close to that in the case of the design of the related art. On the other hand, if the value of $|\xi_0|$ is around $3.0\sigma_{SF}$, the amount of transmission of high-frequency components can be significantly increased, and hence the characteristics of a small-size object or structure can be particularly efficiently transmitted. However, since low-frequency components are significantly reduced, the total amount of signals is often reduced. If $g_S(x_0, y_0)$ has a full width at half maximum of $w_S$, the relation $w_S = 2\sigma_S(2 \ln 2)^{0.5}$ is satisfied when $g_S(x_0, y_0)$ has a Gaussian shape. Therefore, expression (27) can be rewritten as follows:

$$0.3\frac{\sqrt{2\ln 2}}{\pi w_S} \frac{L_{01}}{L_{12}} < |\xi_0| < 3.0\frac{\sqrt{2\ln 2}}{\pi w_S} \frac{L_{01}}{L_{12}}. \qquad (28)$$

This can be roughly rewritten as follows by calculating coefficient parts and using $\alpha_1$:

$$0.1\frac{d_{IP}}{w_S} \frac{L_{01}}{L_{12}} < |\alpha_1| < 1.1\frac{d_{IP}}{w_S} \frac{L_{01}}{L_{12}}. \qquad (29)$$

Expression (29) gives a suitable range of the deviation ratio $\alpha_1$ for determining the pitch $d_0$ of the source grating 2 in the present embodiment. If the emission intensity distribution $g_S(x_0, y_0)$ of the X-ray emitting spot 1 has a typical shape (e.g., the shape of a rectangular function) other than the Gaussian shape, a suitable range of $\alpha_1$ substantially coincides with the range given by expression (29) while the shape of $H_S(\xi, \eta)$ becomes more complex.

The relation between $d_{IP}$ and $d_1$, which is the grating period of the beam splitter grating 3, can be generally written as follows:

$$d_{IP} = \frac{d_1}{m} \frac{L_{01} + L_{12}}{L_{01}} \qquad (30)$$

where m is a positive integer. A suitable value of m is determined by the relation between the pattern of the beam splitter grating 3 and the interference patterns, but m may generally be 1 or 2. A typical example of the case of m=1 is the case of using a so-called π/2 phase modulation grating as the beam splitter grating 3. A typical example of the case of m=2 is the case of using a so-called π phase modulation grating as the beam splitter grating 3. Using harmonic components in the interference patterns as a carrier wave also corresponds to the case where m has a value other than 1. By using equation (30), expression (29) can be rewritten as follows using $d_1$:

$$0.1\frac{d_1}{mw_S} \frac{L_{01} + L_{12}}{L_{12}} < |\alpha_1| < 1.1\frac{d_1}{mw_S} \frac{L_{01} + L_{12}}{L_{12}}. \qquad (31)$$

The value of $d_0$ in this case can be rewritten as follows using $d_1$:

$$d_0 = \frac{n_1 d_1}{m} \frac{L_{01} + L_{12}}{L_{12}} (1 + \alpha_1). \qquad (32)$$

Additionally, $d_2$ can be rewritten as follows:

$$d_2 = \frac{n_2 d_1}{m} \frac{L_{01} + L_{12}}{L_{01}} \qquad (33)$$

where $n_2$ is a positive integer, which may be 1 ($n_2=1$) for higher transmittance.

The emission intensity distribution of the X-ray emitting spot 1 is known to be easily measured, for example, by performing imaging with a pinhole placed at a predetermined position in the X-ray path. The full width at half maximum of the emission intensity distribution, $w_S$, can be easily measured. Therefore, it is easy to determine whether the interferometer satisfies expressions (31) and (32).

Of components of the sidebands appearing in $G_{IPo}(\xi, \eta)$, the components of the upper sideband may be strongly transmitted by setting $\alpha_1<0$, or the components of the lower sideband may be strongly transmitted by setting $\alpha_1>0$. However, as described above, the object information appears not only as the amplitude modulation of the interference patterns, but also as the phase modulation of the interference patterns. Therefore, generally, the amplitude spectrum of the upper sideband and the amplitude spectrum of the lower sideband are not perfectly symmetrical. Also, depending on the type of the object, the visibility and detectability of the structure may vary significantly, in accordance with which of the upper and lower sideband components are transmitted. Therefore, on the basis of this relation, the value of $\alpha_1$ may be set such that, in a sideband predicted in advance, a region to be transmitted (enhanced) is located near a maximum value in a region of the frequency filter $H_S$ applied to the carrier wave. The interferometer may have a configuration which allows the user to set the size of the object the user particularly wants to observe (enhance). In this case, the interferometer may include a setting unit for the user to set the size, a computing device, and a positioning unit for positioning a determined one of a plurality of source gratings in the optical path. The computing device may include a first unit configured to determine a frequency to be enhanced on the basis of the set size, a second unit configured to determine $\alpha_1$ in accordance with the frequency difference ($\xi_0$) between the determined frequency and a carrier wave, and a third unit configured to determine the source grating to be used on the basis of the determined $\alpha_1$. The setting unit may be, for example, a display unit configured to display a dial or buttons for entry of numerical values and also display a set numerical value. The positioning unit for positioning a determined source grating in the optical path may be a moving unit (e.g., actuator or gear) configured to move the source grating in response to a command from the computing device. Instead of selecting a source grating to be used from a plurality of source gratings, a source grating having a variable pitch (e.g., a source grating described in Japanese Patent Laid-Open No. 2011-153869) may be used.

Instead of using a source grating, an X-ray source having a one-dimensional or two-dimensional array of linear X-ray emitting portions or small X-ray emitting spots may be used. This X-ray source may be produced by texturing the anode surface of an X-ray tube or arranging an array of anode materials in the X-ray tube, or by forming an array pattern on a normal anode surface with electron beams from an electron optical system. The interferometer may be configured to vary the shape of electron beams by controlling the electron optical system. This can change the period of the array of linear X-ray emitting portions or small X-ray emitting spots, and thus can easily change a spatial frequency to be particularly enhanced in the object information.

When the interferometer is configured such that the positional relation between the interference patterns and the analyzer grating can be changed, the imaging technique can be selected or changed and executed, in accordance with the object or information to be acquired. If this positional relation can be changed, it is possible to perform not only an imaging technique which does not involve fringe analysis, but also an imaging technique which involves analysis of acquired moire fringes to obtain object information. When fringe analysis is performed, moire fringes with a relatively short period may be formed on the detector, or a detection result may be obtained by a phase stepping technique (fringe scanning technique). The object information obtained by fringe analysis is typically a distribution, in the acquired moire fringes, of local average values excluding intensity fluctuations caused by moire, local phase values of specific moire fringe components, and local visibility values of the specific moire fringe components. The visibility value of a moire fringe component is often defined as a value obtained by dividing the amplitude of a periodic component of moire fringes by an average value.

To configure the interferometer such that the positional relation between the interference patterns and the analyzer grating can be changed, the interferometer may include a moving unit capable of moving at least one of the source grating, the beam splitter grating, and the analyzer grating. The interference patterns can be moved by moving at least one of the source grating and the beam splitter grating.

The moving unit may be, for example, an actuator. The imaging technique to be used may be determined when the operator specifies the amount of movement as an instruction to the moving unit. Gratings may be automatically positioned in response to selection of an imaging mode by the operator. For automatic positioning of gratings in response to selection of an imaging mode by the operator, the interferometer may include an imaging mode instruction unit configured to give the selected imaging mode as an instruction to a movement instruction unit, and the movement instruction unit configured to give the amount of movement as an instruction to the moving unit for each grating. The movement instruction unit gives, to the moving unit for each grating, the amount of movement of the grating for appropriate positioning of the grating. The movement of a grating includes in-plane rotation of the grating. The imaging mode instruction unit and the movement instruction unit may each be formed by a computing device including a processor and a storage unit. The imaging mode instruction unit and the movement instruction unit may be formed as a single computing device. The imaging mode instruction unit, the movement instruction unit, and the object information acquiring unit may be formed as a single computing device.

In the case of executing an imaging mode which involves forming moire fringes with a relatively short period on the detector and acquiring the intensity distribution of the moire fringes to perform fringe analysis, the moire fringes may have a pitch that is 2 to 20 times the pixel pitch of detection pixels. Thus, when the movement instruction unit receives an instruction to execute this imaging mode, the source grating, the beam splitter grating, and the analyzer grating are arranged such that the pitch of the moire fringes falls within this range in the absence of any object between the source grating and the detector. This imaging mode can be executed by performing imaging, with the gratings arranged as described above.

In the case of executing an imaging mode which involves performing a phase stepping technique, it is required to vary the positional relation between a periodic pattern formed by a plurality of interference patterns and the analyzer grating to detect the X-ray intensity distribution multiple times. Therefore, when the movement instruction unit receives an instruction to execute this imaging mode from the imaging mode instruction unit, the position of at least one of the source grating, the beam splitter grating, and the analyzer grating is changed during multiple acquisitions of the X-ray intensity distribution. Instead of selecting an imaging mode, the operator may select, for example, the period of a periodic pattern, and the periodic direction of the periodic pattern or of the grating pattern of the analyzer grating.

Although the above-described embodiment deals with a one-dimensional grating having a periodic direction in one direction, a two-dimensional grating having periods in a plurality of directions may be used. For example, when a two-dimensional grating having periodic direction in the x-axis and y-axis directions is used, it is only necessary that expressions (31), (32), and (33) be satisfied in both the x-axis and y-axis directions. The same applies to the case of using a two-dimensional grating (e.g., hexagonal grating) having periodic directions in three or more directions.

A more concrete example of the present embodiment will now be described.

EXAMPLE 1

Example 1 is a concrete example of the present embodiment. As the X-ray source, the interferometer includes an X-ray tube having a tungsten anode. The X-ray tube is configured to emit X-rays having a certain energy bandwidth, with a photon energy of about 25 keV at the center, by controlling the tube voltage or a filter. The present interferometer is designed to function effectively particularly for X-rays having a wavelength of about 0.05 nm (i.e., a photon energy of about 25 keV). The effective emission intensity distribution of the X-ray emitting spot has a two-dimensional Gaussian shape with a full width at half maximum of 500 μm. The patterns of the source grating, the beam splitter grating, and the analyzer grating are as illustrated in FIGS. 2A to 2C. The beam splitter grating is a silicon phase grating with a grating period $d_1$ of 8.0 μm. Since the grating substrate has a 32 μm difference in thickness between the phase-advance and phase-delay portions, a phase modulation of about π rad is applied to incident X-rays with a wavelength of about 0.05 nm. Note that the phase-advance and phase-delay portions are equal in width. The source grating and the analyzer grating both have a structure in which a gold plating layer of 100 μm thick is formed on a silicon substrate to form X-ray shielding portions. The detector is a flat panel detector having a pixel pitch of 50 μm. A point spread function specific to the detector has a two-dimensional Gaussian shape with a full width at half maximum of 50 μm.

The distances $L_{01}$ and $L_{12}$ are 800 mm and 200 mm, respectively. The source grating and the X-ray emitting spot are disposed at substantially the same position, and the analyzer grating and the detection surface of the detector are disposed at substantially the same position. In this case, $d_0$ and $d_2$ are calculated as $20.0(1+\alpha_1)$ μm and 5.0 μm, respectively, on the basis of equations (32) and (33). Here, m=2 and $n_1=n_2=1$ are set by taking into account that the beam splitter grating is a so-called π phase modulation grating. In the present example, the deviation ratio $\alpha_1$ is set to −0.015. This means that $d_0$ is 19.7 μm. The value of $\alpha_1$ may be in the range of $0.004<|\alpha_1|<0.044$ on the basis of expression (31).

An aspect of the present invention can provide an X-ray Talbot interferometer that is capable of acquiring scattering information, and also acquiring phase information with higher sensitivity than a Talbot interferometer of the related art which performs the dark-field technique.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-155461 filed Aug. 5, 2015, which is hereby incorporated by reference herein in its entirety.

What is claimed is:

1. An X-ray Talbot interferometer comprising:
   a source grating having a plurality of X-ray transmitting portions to transmit some X-rays from an X-ray source;
   a beam splitter grating configured to diffract the X-rays from the X-ray transmitting portions with a periodic structure to form interference patterns;
   an analyzer grating configured to block parts of the interference patterns; and
   a detector configured to detect X-rays from the analyzer grating,
   wherein the beam splitter grating forms the interference patterns corresponding to the respective X-ray transmitting portions by diffracting X-rays from each of the X-ray transmitting portions with the periodic structure;
   the X-ray transmitting portions are arranged to form a periodic pattern in which specific spatial frequency components are enhanced by superimposing the interference patterns corresponding to the respective X-ray transmitting portions;
   the specific spatial frequency components are spatial frequency components contained in a sideband produced when spatial frequency components specific to the interference patterns are modulated by an object; and
   when no object is placed between the source grating and the analyzer grating, the periodic pattern is is substantially the same as a grating pattern of the analyzer grating in a positional relationship over an entire imaging field.

2. The X-ray Talbot interferometer according to claim 1, wherein a pitch of the interference patterns is the same as a pitch of the analyzer grating, and a periodic direction of the interference patterns is the same as a periodic direction of the analyzer grating.

3. The X-ray Talbot interferometer according to claim 1, wherein the imaging field corresponds to an entire detection surface of the detector.

4. The X-ray Talbot interferometer according to claim 1,
   wherein a pitch of the periodic pattern is the same as a pitch of the analyzer grating;
   the source grating, the beam splitter grating, and the analyzer grating are arranged such that when no object is placed between the source grating and the detector, a smaller one of two distances in a periodic direction of the periodic pattern, one distance being a distance between a center of each bright portion of the periodic pattern and a center of the corresponding X-ray shielding portion of the analyzer grating and the other distance being a distance between a center of each bright portion of the periodic pattern and a center of the corresponding X-ray transmitting portion of the analyzer grating, is less than or equal to ¼ times the pitch of the periodic pattern.

5. The X-ray Talbot interferometer according to claim 4, wherein
   the source grating, the beam splitter grating, and the analyzer grating are arranged such that the smaller one of two distances is less than or equal to ⅛ times the pitch of the periodic pattern.

6. The X-ray Talbot interferometer according to claim 4, wherein the source grating, the beam splitter grating, and the analyzer grating are arranged such that the smaller one of the two distances is less than or equal to ¹⁄₁₀ times the pitch of the periodic pattern.

7. The X-ray Talbot interferometer according to claim 5, wherein m is 1 or 2.

8. The X-ray Talbot interferometer according to claim 1, wherein the source grating, the beam splitter grating, and the analyzer grating are each a grating having a grating pattern containing a plurality of periodic components in different directions.

9. The X-ray Talbot interferometer according to claim 1, further comprising:
   a moving unit configured to move a position of at least one of the source grating, the beam splitter grating, and the analyzer grating; and
   an imaging mode instruction unit configured to give an instruction indicating an imaging mode to be executed,
   wherein the imaging mode instruction unit is capable of indicating a first imaging mode and a second imaging mode;
   the first imaging mode is an imaging mode in which imaging is performed when the positional relation between the periodic pattern and the grating pattern of the analyzer grating, in the absence of any object between the source grating and the analyzer grating, is substantially the same over the entire imaging field; and
   the second imaging mode is an imaging mode in which a phase stepping technique is performed.

10. The X-ray Talbot interferometer according to claim 1, further comprising a moving unit configured to move a position of at least one of the source grating, the beam splitter grating, and the analyzer grating,
    wherein the detector has a plurality of detection pixels configured to detect X-rays;
    an imaging mode can be changed from a first imaging mode to a second imaging mode or from the second imaging mode to the first imaging mode when the moving unit changes a positional relation between the interference patterns and the analyzer grating;

the first imaging mode is an imaging mode in which imaging is performed when the positional relation between the periodic pattern and the grating pattern of the analyzer grating, in the absence of any object between the source grating and the analyzer grating, is substantially the same over the entire imaging field; and the second imaging mode is an imaging mode in which imaging is performed in a state where the source grating, the beam splitter grating, and the analyzer grating are arranged such that, in the absence of any object between the source grating and the analyzer grating, an intensity distribution having a period that is 2 to 20 times a pixel pitch of the detection pixels is formed in the imaging field.

11. The X-ray Talbot interferometer according to claim 1, further comprising the X-ray source.

12. The X-ray Talbot interferometer according to claim 1, further comprising an image display unit configured to display an X-ray intensity distribution acquired by the detector.

13. An X-ray Talbot interferometer comprising:
a source grating having a plurality of X-ray transmitting portions to transmit some X-rays from an X-ray source;
a beam splitter grating configured to diffract the X-rays from the X-ray transmitting portions with a periodic structure to form interference patterns;
an analyzer grating configured to block parts of the interference patterns; and
a detector configured to detect X-rays from the analyzer grating,
wherein the beam splitter grating forms the interference patterns corresponding to the respective X-ray transmitting portions by diffracting X-rays from each of the X-ray transmitting portions with the periodic structure;
the X-ray transmitting portions are arranged to form a periodic pattern in which specific spatial frequency components are enhanced by superimposing the interference patterns corresponding to the respective X-ray transmitting portions;
a pitch of the interference patterns is the same as a pitch of the analyzer grating, and a periodic direction of the interference patterns is the same as a periodic direction of the analyzer grating; and
a pitch $d_0$ of the X-ray transmitting portions of the source grating is expressed by the following equation:

$$d_0 = \frac{n_1 d_1}{m} \frac{L_{01} + L_{12}}{L_{12}} (1 + \alpha_1)$$

where $d_1$ is a grating pitch of the beam splitter grating, $n_1$ and $m$ are positive integers, $L_{01}$ is a distance between the source grating and the beam splitter grating, $L_{12}$ is a distance between the beam splitter grating and the analyzer grating, and $\alpha_1$ is a constant that is in the following range:

$$0.1 \frac{d_1}{m w_S} \frac{L_{01} + L_{12}}{L_{12}} < |\alpha_1| < 1.1 \frac{d_1}{m w_S} \frac{L_{01} + L_{12}}{L_{12}}$$

where $w_S$ is a full width at half maximum of an emission intensity distribution of X-ray emitting spot in the X-ray source.

14. The X-ray Talbot interferometer according to claim 13,
wherein a pitch of the periodic pattern is the same as the pitch of the analyzer grating;
the source grating, the beam splitter grating, and the analyzer grating are arranged such that when no object is placed between the source grating and the detector, a smaller one of two distances in a periodic direction of the periodic pattern, one distance being a distance between a center of each bright portion of the periodic pattern and a center of the corresponding X-ray shielding portion of the analyzer grating and the other distance being a distance between a center of each bright portion of the periodic pattern and a center of the corresponding X-ray transmitting portion of the analyzer grating, is less than or equal to ¼ times the pitch of the periodic pattern.

15. The X-ray Talbot interferometer according to claim 14,
wherein
the source grating, the beam splitter grating, and the analyzer grating are arranged such that the smaller one of two distances is less than or equal to ⅛ times the pitch of the periodic pattern.

16. The X-ray Talbot interferometer according to claim 15, wherein the source grating, the beam splitter grating, and the analyzer grating are arranged such that the smaller one of the two distances is less than or equal to 1/10 times the pitch of the periodic pattern.

17. The X-ray Talbot interferometer according to claim 13, wherein the source grating, the beam splitter grating, and the analyzer grating are each a grating having a grating pattern containing a plurality of periodic components in different directions.

18. The X-ray Talbot interferometer according to claim 13, further comprising:
a moving unit configured to move a position of at least one of the source grating, the beam splitter grating, and the analyzer grating; and
an imaging mode instruction unit configured to give an instruction indicating an imaging mode to be executed,
wherein the imaging mode instruction unit is capable of indicating a first imaging mode and a second imaging mode;
the first imaging mode is an imaging mode in which imaging is performed when a positional relation between the periodic pattern and a grating pattern of the analyzer grating, in the absence of any object between the source grating and the analyzer grating, is substantially the same over an entire imaging field; and
the second imaging mode is an imaging mode in which a phase stepping technique is performed.

19. The X-ray Talbot interferometer according to claim 13, further comprising a moving unit configured to move a position of at least one of the source grating, the beam splitter grating, and the analyzer grating,
wherein the detector has a plurality of detection pixels configured to detect X-rays;
an imaging mode can be changed from a first imaging mode to a second imaging mode or from the second imaging mode to the first imaging mode when the moving unit changes a positional relation between the interference patterns and the analyzer grating;
the first imaging mode is an imaging mode in which imaging is performed when a positional relation between the periodic pattern and a grating pattern of the analyzer grating, in the absence of any object between the source grating and the analyzer grating, is substantially the same over an entire imaging field; and the second imaging mode is an imaging mode in which imaging is performed in a state where the source grating, the beam splitter grating, and the analyzer grating are arranged such that, in the absence of any object between the source grating and the analyzer grating, an intensity distribution having a period that is 2 to 20 times a pixel pitch of the detection pixels is formed in the imaging field.

20. The X-ray Talbot interferometer according to claim 13, further comprising the X-ray source.

21. The X-ray Talbot interferometer according to claim 13, further comprising an image display unit configured to display an X-ray intensity distribution acquired by the detector.

* * * * *